(12) United States Patent
Cleland et al.

(10) Patent No.: US 8,501,216 B2
(45) Date of Patent: *Aug. 6, 2013

(54) BIOERODIBLE POLYMERS FOR INJECTION

(75) Inventors: Jeffrey L. Cleland, San Carlos, CA (US); Franklin Okumu, Oakland, CA (US)

(73) Assignee: Genentech, Inc., South San Francisco, CA (US)

( * ) Notice: Subject to any disclaimer, the term of this patent is extended or adjusted under 35 U.S.C. 154(b) by 309 days.

This patent is subject to a terminal disclaimer.

(21) Appl. No.: 12/823,027

(22) Filed: Jun. 24, 2010

(65) Prior Publication Data

US 2011/0152190 A1    Jun. 23, 2011

Related U.S. Application Data

(63) Continuation of application No. 10/080,502, filed on Feb. 22, 2002, now Pat. No. 7,824,700.

(60) Provisional application No. 60/270,845, filed on Feb. 23, 2001.

(51) Int. Cl.
   *A61F 2/02*    (2006.01)
(52) U.S. Cl.
   USPC ........................................................ 424/426
(58) Field of Classification Search
   None
   See application file for complete search history.

(56) References Cited

U.S. PATENT DOCUMENTS

| | | | |
|---|---|---|---|
| 4,297,344 A | 10/1981 | Schwinn et al. |
| 4,938,763 A | 7/1990 | Dunn et al. |
| 4,975,271 A | 12/1990 | Dunn et al. |
| 5,019,400 A | 5/1991 | Gombotz et al. |
| 5,077,049 A | 12/1991 | Dunn et al. |
| 5,096,885 A | 3/1992 | Pearlman et al. |
| 5,133,981 A | 7/1992 | Harkrader et al. |
| 5,242,910 A | 9/1993 | Damanj |
| 5,278,201 A | 1/1994 | Dunn et al. |
| 5,278,202 A | 1/1994 | Dunn et al. |
| 5,324,519 A | 6/1994 | Dunn et al. |
| 5,324,520 A | 6/1994 | Dunn et al. |
| 5,340,849 A | 8/1994 | Dunn et al. |
| 5,368,859 A | 11/1994 | Dunn et al. |
| 5,487,897 A | 1/1996 | Polson et al. |
| 5,556,905 A | 9/1996 | Frappier et al. |
| 5,589,167 A | 12/1996 | Cleland et al. |

(Continued)

FOREIGN PATENT DOCUMENTS

| CA | 2324265 A | 9/1999 |
|---|---|---|
| EP | 0 216 485 | 4/1987 |

(Continued)

OTHER PUBLICATIONS

Arakawa et al. (1991). "Protein-Solvent Interactions in Pharmaceutical Formulations," *Pharmaceutical Research* 8(3):285-291.

(Continued)

*Primary Examiner* — Carlos Azpuru
(74) *Attorney, Agent, or Firm* — Morrison & Foerster LLP (57) ABSTRACT

A composition for administration of a beneficial agent, contains a solvent mixture including a hydrophobic solvent and a hydrophilic solvent; a bioerodible polymer; and a beneficial agent. The polymer and the beneficial agent are dissolved. The composition has a low viscosity, allowing for easy injection through standard hypodermic needles.

48 Claims, 6 Drawing Sheets

U.S. PATENT DOCUMENTS

| | | | |
|---|---|---|---|
| 5,591,713 | A | 1/1997 | Igari et al. |
| 5,599,552 | A | 2/1997 | Dunn et al. |
| 5,651,986 | A | 7/1997 | Brem et al. |
| 5,665,394 | A | 9/1997 | Igari et al. |
| 5,747,058 | A | 5/1998 | Tipton et al. |
| 5,780,044 | A | 7/1998 | Yewey et al. |
| 5,783,205 | A | 7/1998 | Berggren et al. |
| 5,912,015 | A | 6/1999 | Bernstein et al. |
| 5,945,115 | A | 8/1999 | Dunn et al. |
| 5,972,370 | A | 10/1999 | Eckenhoff et al. |
| 5,980,945 | A | 11/1999 | Ruiz |
| 6,007,845 | A | 12/1999 | Domb et al. |
| 6,039,977 | A | 3/2000 | Venkatraman et al. |
| 6,051,259 | A | 4/2000 | Johnson et al. |
| 6,066,619 | A | 5/2000 | Stevenson et al. |
| 6,080,429 | A | 6/2000 | Cleland et al. |
| 6,087,324 | A | 7/2000 | Igari et al. |
| 6,110,503 | A | 8/2000 | Rickey et al. |
| 6,113,943 | A | 9/2000 | Okada et al. |
| 6,113,947 | A | 9/2000 | Cleland et al. |
| 6,120,789 | A | 9/2000 | Dunn |
| 6,124,261 | A | 9/2000 | Stevenson et al. |
| 6,130,200 | A | 10/2000 | Brodbeck et al. |
| 6,143,314 | A | 11/2000 | Chandrashekar et al. |
| 6,146,662 | A | 11/2000 | Jao et al. |
| 6,165,508 | A | 12/2000 | Tracy et al. |
| 6,174,547 | B1 | 1/2001 | Dong et al. |
| 6,190,700 | B1 | 2/2001 | Okada et al. |
| 6,191,107 | B1 | 2/2001 | Yamagata et al. |
| 6,197,350 | B1 | 3/2001 | Yamagata et al. |
| 6,331,311 | B1 | 12/2001 | Brodbeck et al. |
| 6,372,245 | B1 | 4/2002 | Bowman et al. |
| 6,468,961 | B1 | 10/2002 | Brodbeck et al. |
| 7,824,700 | B2 | 11/2010 | Cleland et al. |
| 2002/0034532 | A1 | 3/2002 | Brodbeck et al. |
| 2002/0173552 | A1 | 11/2002 | Cleland et al. |
| 2003/0044467 | A1 | 3/2003 | Brodbeck et al. |

FOREIGN PATENT DOCUMENTS

| | | | |
|---|---|---|---|
| EP | 0 467 389-81 | | 1/1992 |
| EP | 0 484 387-81 | | 1/1994 |
| EP | 0 949 905 | | 7/2001 |
| JP | 8-505139 | T | 6/1996 |
| JP | 2004-511431 | T | 4/2004 |
| MX | 173182 | A | 7/1994 |
| WO | WO-89/03671 | | 5/1989 |
| WO | WO-92/17200 | | 10/1992 |
| WO | WO-97/26015 | | 7/1997 |
| WO | PCT/US97/23659 | * | 12/1997 |
| WO | WO-98/27962 | | 7/1998 |
| WO | WO-98/27963 | | 7/1998 |
| WO | WO-99/47073 | | 9/1999 |
| WO | WO-00/78335 | | 12/2000 |
| WO | WO-02/00137 | A1 | 1/2002 |
| WO | WO-03/041684 | | 5/2003 |
| WO | WO-03/041757 | | 5/2003 |

OTHER PUBLICATIONS

Gray et al. (1990). "Cloning of Human Tumor Necrosis Factor (TNF) Receptor cDNA and Expression of Recombinant Soluble TNF-Binding Protein," *Proc. Natl. Acad. Sci. USA* 87:7380-7381.

Hawley's Medical Dictionary (2002). "Emulsion," 14$^{th}$ Edition.

International Search Report mailed Aug. 22, 2002, for PCT Application No. PCT/US02/05445, filed Feb. 22, 2002, two pages.

Israeli Office Action for Application No. 157531 dated Jul. 25, 2007, two pages (English Translation Only.).

Johnson et al. (1996). "A Month-Long Effect from a Single Injection of Microencapsulated Human Growth Hormone," *Nature Medicine* 2(7):795-799.

Kita et al. (1994). "Contribution of the Surface Free Energy Perturbation to Protein-Solvent Interactions," *Biochemistry* 33:15178-15189.

Kohno et al. (1990). "A Second Tumor Necrosis Factor Receptor Gene Product can Shed a Naturally Occurring Tumor Necrosis Factor Inhibitor," *Proc. Natl. Acad. Sci. USA* 87:8331-8335.

Lai et al. (1998). (1998). "Metal and RNA Binding Properties of the hdm2 RING Finger Domain," *Biochemistry* 37(48):17005-17015.

Life Science Dictionary (1995-1998). "Emulsion."

Lin et al. (1996). (1996). "On the Role of Surface Tension in the Stabilization of Globular Proteins," *Protein Science* 5:372-381.

Maa et al. (1998). "Spray-Drying of Air-Liquid Interface Sensitive Recombinant Human Growth Hormone," *Journal of Pharmaceutical Sciences* 87(2):152-159.

Sackett et al. (1998). "Multivalent Cations Depress Ligand Binding to Cell-Associated Insulin-Like Growth Factor Binding Protein-5 on Human Glioblastoma Cells," *Endocrinology* 139(4):1943-1951.

Smith et al. (1996). "A Novel Parenteral Delivery System," Pharmaceutical Research PDD 7270, 13(3) one page.

Timasheff, S.N. (1993). "The Control of Protein Stability and Association by Weak Interactions with Water: How do Solvents Affect These Processes?" *Annu. Rev. Biophys. Biomol. Struct.* 22:67-97.

Timasheff, S.N. (1995). "Solvent Stabilization of Protein Structure," *Methods in Molecular Biology* 40:253-269.

Timasheff, S.N. (1998). "Control of Protein Stability and Reactions by Weakly Interacting Cosolvents: The Simplicity of the Complicated," *Advances in Protein Chemistry* 51:355-432.

Xie et al. (1997). "The Thermodynamic Mechanism of Protein Stabilization by Trehalose," *Biophysical Chemistry* 64:25-43.

Yang et al. (2000). "Effect of Zinc Binding and Precipitation on Structures of Recombinant Human Growth Hormone and Nerve Growth Factor," *Journal of Pharmaceutical Sciences* 89(11)::1480-1485.

* cited by examiner

BIOERODIBLE POLYMERS FOR INJECTION

CROSS-REFERENCE TO RELATED APPLICATIONS

This application is a continuation application of U.S. patent application Ser. No. 10/080,502, filed Feb. 22, 2002, which claims the benefit of U.S. Provisional Application No. 60/270,845, filed Feb. 23, 2001, each of which is incorporated herein by reference.

BACKGROUND

Controlled delivery of beneficial agents, especially peptide- and protein-based drug therapies, can be achieved through the use of bioerodible polymeric implants. Traditionally, this technology has involved surgical implantation of a polymeric monolith containing a suspended beneficial agent. Examples of these monoliths are described in U.S. Pat. Nos. 6,110,503, 6,051,259, and 6,146,662. Certain complex shapes and/or formulations of these monoliths have been developed to provide specific rates of release of the beneficial agent over a period of time. A drawback to this implantation approach is the need to perform an incision in the patient in order to place the implant.

In order to eliminate the need for surgical implantation, implants have been developed which can be administered by the injection of a viscous composition. Compositions for injection must have a sufficient ability to flow so that the implant can pass through a syringe and needle. However, these formulations should not simply dissipate into the body but rather should form a discrete depot from which the drug is released. Typically, the composition transforms into a solid or a gel upon encountering the aqueous environment within an organism.

To accomplish this balance of physical properties, various formulations of bioerodible polymers, biocompatible solvents, beneficial agents, and other ingredients have been employed. Release of the beneficial agent from the polymeric matrix of the implant can then occur by: diffusion of the agent from the matrix; by degradation of the polymer and subsequent release of the agent into the surrounding environment; or by a combination of these two mechanisms.

One approach to the formulation of injectable compositions has been the use of solvents which are miscible or dispersible with water (hydrophilic solvents). For example, U.S. Pat. No. 6,143,314 describes injectable compositions containing poly(lactic acid-co-glycolic acid) (PLGA) and a hydrophilic solvent such as dimethyl sulfoxide (DMSO) or N-methyl pyrrolidone (NMP). U.S. Pat. Nos. 5,278,201 and 4,938,763 describe poly(lactic acid), poly(glycolic acid), and their copolymers combined with NMP and a beneficial agent to form injectable liquid compositions. Depots of these same polymers also can be formed by injecting a composition containing a prepolymer, which then forms the polymer during the implantation process. As described in U.S. Pat. Nos. 5,340,849 and 5,278,202, compositions of NMP, a beneficial agent, and polymer precursors can form a polymer gel upon injection into an aqueous environment due to polymerization of the polymer precursors in the presence of water.

The beneficial agent can be either dissolved or dispersed in these formulations. Water-soluble beneficial agents, including peptides and proteins, are typically dissolved by the solvents which are miscible in aqueous body fluids. The solvents used in these compositions tend to provide for the rapid influx of water into the implant. This promotes rapid solidification of the polymer at the implant surface and promotes diffusion of the beneficial agent from the implant, often resulting in an initial, rapid release of the beneficial agent. This "burst" often results in the release of a substantial portion of the beneficial agent within a very short time. For example, 25-75% of the beneficial agent can be released within 24 hours of administration. In some cases, the burst can be followed by a drastic reduction in the release of the beneficial agent before a gradual release begins. This pause in the release behavior is referred to as a "lag time."

A burst effect and/or lag time can be unacceptable, particularly in circumstances where sustained delivery is desired. For example, it may be desirable to deliver the beneficial agent over a period of a week or a month or longer. To control release rates of these systems, it is often necessary to include additional ingredients which can moderate the release of the beneficial agent and/or control the porosity of the implant. For example, U.S. Pat. Nos. 5,599,552 and 5,487,897 describe complex compositions which use poly(D,L-lactic acid) to provide an implant that has a porous or liquid core surrounded by a layer, or "skin," of polymer. This morphology is reported to provide for a more uniform release rate. Release of a beneficial agent can also be controlled by complexing the agent to make it less soluble in water, as described in U.S. Pat. No. 5,780,044; however, complexation can affect the activity, and thus the efficacy, of the beneficial agent.

An alternative approach to the formulation of controlled release compositions has been the use of solvents which are immiscible with water. For example, U.S. Pat. No. 6,130,200 describes gels of PLGA and a water-immiscible (hydrophobic) solvent in which peptide-based drugs are suspended as particles. When administered, the gels have sufficient dimensional stability to form a cohesive depot. The hydrophobic solvent in these systems inhibits the rapid uptake of water, resulting in the reduction or elimination of any burst release. One drawback to this system is the high viscosities exhibited by the gels. Large diameter needles (16-gauge to 20-gauge) must be employed to administer the composition by injection, and high pressures are necessary for administration. This can be especially disadvantageous in the treatment of chronic conditions, such as the administration of insulin to diabetic patients. Another drawback is the tendency of the particulate beneficial agent to settle out of the composition over time. This instability can necessitate special storage conditions, short storage times, and/or special handling conditions during administration. If the beneficial agent settles out once the implant is in the organism, the rate of release of the agent over time can become unpredictable.

There is thus a need for compositions for the gradual release of a beneficial agent which can be easily administered by injection. These compositions will ideally exhibit controlled release of the agent, without unintended periods of rapid release or zero release. Additionally, stability for long periods of time and under various storage conditions would be desirable.

BRIEF SUMMARY

In a first aspect, the present invention is a composition for administration of a beneficial agent, containing: a solvent mixture including a hydrophobic solvent and a hydrophilic solvent; a bioerodible polymer; and a beneficial agent. The polymer and the beneficial agent are dissolved.

In a second aspect, the present invention is a composition for administration of a beneficial agent, containing: a solvent mixture including a hydrophobic solvent and a hydrophilic solvent; a bioerodible polymer; and a beneficial agent. The viscosity of the composition is less than 2000 centipoise.

In a third aspect, the present invention is a composition for administration of a beneficial agent, containing: a solvent mixture including a hydrophobic solvent and a hydrophilic solvent; a bioerodible polymer dissolved in the solvent mixture; and a beneficial agent dissolved in the solvent mixture. The viscosity of the composition is less than 2000 centipoise, at least 90 wt % of the solvent mixture is the hydrophobic solvent, the hydrophobic solvent has a solubility in water of less than 0.1 wt %, and less than 5% of the beneficial agent is released in 24 hours following administration in vivo.

In a fourth aspect, the present invention is a method of administering a beneficial agent, including injecting the above compositions into an organism through a needle.

In a fifth aspect, the present invention is a kit containing a container; a hydrophobic solvent; a hydrophilic solvent; a bioerodible polymer; and a beneficial agent. The amount of the hydrophobic solvent and the hydrophilic solvent is sufficient together to dissolve all of the polymer and the beneficial agent.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein.

DETAILED DESCRIPTION

The present invention includes a solution of a bioerodible polymer dissolved in a mixed solvent system containing at least two solvents. The polymer solution is mixed with a beneficial agent to form a liquid or gel which can be injected into an organism, preferably using a needle having a diameter no greater than that of a 20-gauge needle. The beneficial agent is then slowly released from the composition into the organism. Compositions can be prepared and administered to provide for continual release of a beneficial agent over a period of time with minimal burst release upon injection. The compositions of the invention are especially useful for peptide- and protein-based beneficial agents. The solution of polymer in the solvent mixture preferably provides for stabilization of the beneficial agent during storage and during the release period.

The mixed solvent system dissolves both the polymer and the beneficial agent. Preferably, the composition is a solution, which means a liquid having multiple ingredients homogeneously distributed in a single phase. Alternatively, the composition may be an suspension of the beneficial agent. Both solutions and suspensions are contrasted with emulsions, which have more than one liquid phase.

It is preferred that the solvents in the solvent mixture exhibit different levels of solubility in water. The solvent which is less soluble in water is called the hydrophobic solvent, and the solvent which is more soluble in water is called the hydrophilic solvent.

Water solubility may be determined experimentally as follows: five grams of water are placed in a clear container at 20° C. and weighed, and a solvent is added dropwise. The solution is swirled to observe phase separation. When the saturation point appears to be reached, as determined by observation of phase separation, the solution is allowed to stand overnight and is checked again the following day. If the solution is still saturated, as determined by observation of phase separation, then the percent by weight of solvent added is determined. Otherwise more solvent is added and the process repeated. Solubility is determined by dividing the total weight of solvent added by the final weight of the solvent/water mixture.

Preferably the hydrophobic solvent accounts for more than half of the mass of the solvent mixture. Useful hydrophobic solvents exhibit a solubility in water less than 1 wt %, preferably less than 0.5 wt %, more preferably less than 0.1 wt %. Especially preferred are hydrophobic solvents having a solubility in water less than 0.05 wt %.

Examples of hydrophobic solvents include the alkyl and aralkyl esters of aryl acids such as benzoic acid, phthalic acid, and salicylic acid; alkyl esters of citric acid, such as triethyl citrate and tributyl citratrate; aryl, aralkyl and alkyl ketones and aldehydes; and mixtures thereof. Among preferred solvents are those having solubilities within the foregoing range selected from (i) compounds having the structural formulas: $R^1$—C(=O)—O—$R^2$ or $R^1$—C(=O)—$R^2$ in which $R^1$ is aryl or aralkyl, $R^2$ is alkyl or aralkyl, and $R^1$ and $R^2$ are optionally the same or different, with the proviso that when each of $R^1$ and $R^2$ are alkyl, the total carbon atoms in $R^1$ and $R^2$ combined are 4 or more, (ii) alkyl and aralkyl esters of phthalic acid, isophthalic acid and terephtalic acid, and (iii) alkyl and aralkyl esters of citric acid. Alkyl means straight, branched, or cyclic hydrocarbons having preferably 1-20 carbon atoms, optionally substituted with non-interfering substituents. Aralkyl means (alkyl)phenyl, for example benzyl, phenethyl, 1-phenylpropyl, and 2-phenylpropyl. Aryl means phenyl, optionally substituted by non-interfering substituents. Many of the solvents useful in the invention are available commercially (SIGMA/ALDRICH, Milwaukee, Wis.) or may be prepared by conventional esterification of the respective arylalkanoic acids using acid halides, and optionally esterification catalysts, such as described in U.S. Pat. No. 5,556,905, and in the case of ketones and aldehydes, by oxidation of their respective alcohol precursors.

Benzoic acid derivatives from which hydrophobic solvents may be selected include: 1,4-cyclohexane dimethanol dibenzoate, diethylene glycol dibenzoate, dipropylene glycol dibenzoate, polypropylene glycol dibenzoate, propylene glycol dibenzoate, diethylene glycol benzoate and dipropylene glycol benzoate blend, polyethylene glycol (200) dibenzoate, iso-decyl benzoate, neo-pentyl glycol dibenzoate, glyceryl tribenzoate, pentaerylthritol tetrabenzoate, cumylphenyl benzoate, trimethyl pentanediol dibenzoate.

Phthalic acid derivatives from which hydrophobic solvents may be selected include: Alkyl benzyl phthalate, bis-cumylphenyl isophthalate, dibutoxyethyl phthalate, dimethyl phthalate, diethyl phthalate, dibutyl phthalate, diisobutyl phthalate, diisoheptyl phthalate, butyl octylphthalate, diisonoyl phthalate, nonyl undecylphthalate, dioctyl phthalate, di-isooctylphthalate, dicapryl phthalate, mixed alcohol phthalate, di-(2-ethylhexyl) phthalate, linear heptyl nonylphthalate, linear heptyl nonyl undecyl phthalate, linear nonyl phthalate, linear nonyl undecylphthalate, linear dinonyl didecylphthalate, diisodecyl phthalate, diundecyl phthalate, ditridecyl phthalate, undecyldodecyl phthalate, decyltridecyl phthalate, 1:1 blend of dioctyl and didecyl phthalates, butyl benzyl phthalate, and dicyclohexyl phthalate.

Preferred hydrophobic solvents include the alkyl and aralkyl esters of the aryl acids described above. Examples of acids are benzoic acid and the phthalic acids, such as phthalic acid, isophthalic acid, and terephathalic acid. Most preferred solvents are derivatives of benzoic acid and include, for example, methyl benzoate, ethyl benzoate, n-propyl benzoate, isopropyl benzoate, butyl benzoate, isobutyl benzoate, sec-butyl benzoate, tert-butyl benzoate, isoamyl benzoate and benzyl benzoate, with benzyl benzoate being most especially preferred. Furthermore, mixtures of any of the hydrophobic solvents may also be used.

Hydrophilic solvents useful in solvent mixtures are those solvents that are miscible with the hydrophobic solvent and include, for example benzyl alcohol, methanol, 1-butanol, t-butanol, triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, mineral oil, polybutene, silicone fluid, glylcerin, ethylene glycol, polyethylene glycol, octanol, ethyl lactate, propylene glycol, propylene carbonate, ethylene carbonate, butyrolactone, ethylene oxide, propylene oxide, N-methyl-2-pyrrolidone, 2-pyrrolidone, glycerol formal, methyl acetate, ethyl acetate, methyl ethyl ketone, dimethylformamide, dimethyl sulfoxide, tetrahydrofuran, caprolactam, decylmethylsulfoxide, oleic acid, 1-dodecylazacycloheptan-2-one, and mixtures thereof.

A useful hydrophilic solvent exhibits a solubility in water greater than the hydrophobic solvent with which it is mixed, typically between 1 wt % and up to and including miscibility with water, preferably up to and including 50 wt %, and most preferably up to and including 25 wt %. Especially preferred are hydrophilic solvents having a solubility in water from 2 wt % to 10 wt %.

The solvent mixture may contain more than two solvents. For example, the solvent mixture may contain two or more hydrophobic solvents, two or more hydrophilic solvents, and/or one or more solvents exhibiting a solubility in water which is between those of the specific hydrophilic and hydrophobic solvents. It is preferred that the total amount of solvent or solvents having a solubility in water of less than 1 wt % accounts for at least 55 wt % of the solvent mixture, preferably at least 75 wt % of the mixture, more preferably at least 90 wt % of the solvent mixture.

The polymers for use with the present invention are materials which decompose when placed inside an organism. Bioerodible polymers eliminate the need to remove the implant after the beneficial agent has been released, since the polymer will gradually break down and may be metabolized or excreted from the body. This decomposition can be observed as a decline in the molecular weight of the polymer over time. Polymer molecular weights can be determined by a variety of methods including size exclusion chromatography (SEC), and are generally expressed as weight averages or number averages. A polymer is bioerodible if, when in phosphate buffered saline (PBS) of pH 7.4 and a temperature of 37° C., its weight-average molecular weight is reduced by at least 25% over a period of 6 months as measured by SEC.

Bioerodible polymers which are useful for the present invention include polyesters, such as poly(caprolactone), poly(glycolic acid), poly(lactic acid), and poly(hydroxybutyrate); polyanhydrides, such as poly(adipic anhydride) and poly(maleic anhydride); polydioxanone; polyamines; polyamides; polyurethanes; polyesteramides; polyorthoesters; polyacetals; polyketals; polycarbonates; polyorthocarbonates; polyphosphazenes; poly(malic acid); poly(amino acids); polyvinylpyrrolidone; poly(methyl vinyl ether); poly (alkylene oxalate); poly(alkylene succinate); polyhydroxycellulose; chitin; chitosan; and copolymers and mixtures thereof.

The beneficial agent can be any physiologically or pharmacologically active substance or substances optionally in combination with pharmaceutically acceptable carriers and additional ingredients such as antioxidants, stabilizing agents, etc. that do not substantially adversely affect the advantageous results that may be attained from administration of the beneficial agent. The beneficial agent may be any of the agents which are known to be delivered to the body of a human or an animal. These agents include drug agents, medicaments, vitamins, and nutrients. Included among the types of agents which meet this description are lower molecular weight compounds, proteins, peptides, genetic material, nutrients, vitamins, food supplements, sex sterilants, fertility inhibitors and fertility promoters.

Drug agents which may be delivered by the present invention include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, ocular drugs and synthetic analogs of these species.

Examples of drugs which may be delivered by the composition of the present invention include, prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isoflourophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-S-estradiol, ethinyl estradiol, ethinyl estradiol 3-methyl ether, prednisolone, 17-α-hydroxyprogesterone acetate, 19-norprogesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, mandol, quanbenz, hydrochlorothiazide, ranitidine, flurbiprofen, fenufen, fluprofen, tolmetin, alclofenac, mefenamic, flufenamic, difuinal, nimodipine, nitrendipine, nisoldipine, nicardipine, felodipine, lidoflazine, tiapamil, gallopamil, amlodipine, mioflazine, lisinoipril, enalapril, enalaprilat captopril, ramipril, famotidine, nizatidine, sucralfate, etintidine, tetratolol, minoxidil, chlordiazepoxide, diazepam, amitriptyline, and imipramine.

Preferably, the beneficial agent is a protein or peptide, more preferably a heterologous glycoprotein. Examples of heterologous glycoproteins include molecules such as cytokines and their receptors, as well as chimeric proteins comprising cytokines or their receptors, including, for example tumor necrosis factor alpha and beta, their receptors (TNFR-1; Gray et al., (1990) Proc. Natl. Acad. Sci. USA 87:7380-7384; and TNFR-2; Kohno et al., (1990) Proc. Natl. Acad. Sci. USA 87:8331-8335) and their derivatives; renin; growth hormones, including human growth hormone, bovine growth hormone, methione-human growth hormone, des-phenylalanine human growth hormone, and porcine growth hormone; growth hormone releasing factor (GRF); parathyroid and pituitary hormones; thyroid stimulating hormone; human pancreas hormone releasing factor; lipoproteins; colchicine; prolactin; corticotrophin; thyrotropic hormone; oxytocin; vasopressin; somatostatin; lypressin; pancreozymin; leuprolide; alpha-1-antitrypsin; insulin A-chain; insulin B-chain; proinsulin; follicle stimulating hormone; calcitonin; luteinizing hormone; luteinizing hormone releasing hormone (LHRH); LHRH agonists and antagonists; glucagon; clotting factors such as factor VIIIC, factor IX, tissue factor, and von Willebrands factor; anti-clotting factors such as Protein C; atrial natriuretic factor; lung surfactant; a plasminogen activator other than a tissue-type plasminogen activator (t-PA), for example a urokinase; bombesin; thrombin; hemopoietic growth factor; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; chorionic gonadotropin; gonadotropin releasing hormone; bovine somatotropin; porcine somatotropin; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-$\beta$; platelet-derived growth factor (PDGF); fibroblast growth factor such as aFGF and bFGF; epidermal growth factor (EGF); transforming growth factor (TGF) such as TGF-alpha and TGF-beta, including TGF-$\beta$1, TGF-$\beta$2, TGF-$\beta$3, TGF-$\beta$4, or TGF-$\beta$5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, -gamma, and consensus interferon; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV-1 envelope glycoprotein, gp120, gp160 or fragments thereof; transport proteins; homing receptors; addressins; fertility inhibitors such as the prostaglandins; fertility promoters; regulatory proteins; antibodies and chimeric proteins, such as immunoadhesins; analogs and derivatives of these compounds, and pharmaceutically acceptable salts of these compounds, or their analogs or derivatives.

Beneficial agents can also include chemotherapeutic agents, specifically the local application of such agents to avoid or minimize systemic side effects. Compositions containing chemotherapeutic agents may be injected directly into the tumor tissue for sustained delivery of the chemotherapeutic agent over time. In some cases, particularly after resection of the tumor, the composition may be implanted directly into the resulting cavity or may be applied to the remaining tissue as a coating. Representative chemotherapeutic agents that may be delivered include, for example, carboplatin, cisplatin, paclitaxel, BCNU, vincristine, camptothecin, etopside, cytokines, ribozymes, interferons, oligonucleotides and oligonucleotide sequences that inhibit translation or transcription of tumor genes, functional derivatives of the foregoing, and typically known chemotherapeutic agents such as those described in U.S. Pat. No. 5,651,986.

Further examples of beneficial agents include antibacterial agents such as iodine, sulfonamides, mercurials, bisbiguanides, or phenolics; antibiotics such as tetracycline, neomycin, kanamycin, metronidazole, or clindamycin; anti-inflammatory agents such as aspirin, naproxen, ibuprofen, flurbiprofen, indomethacin, eugenol, or hydrocortisone; immune-suppressive or stimulatory agents such as methotrexate or levamasole; immune reagents such as immunoglobulin or antigens; anesthetic agents such as lidocaine or benzocaine; nutritional agents such as amino acids, essential fats, and vitamin C; and antioxidants such as alphatocopherol and butylated hydroxy toluene. The composition may also contain pharmaceutically acceptable carriers and additional ingredients, and these substances may be dissolved or may be suspended.

The beneficial agent, polymer, and solvent components may be mixed together in one step or may be mixed together in separate steps, in any order. It is preferred to dissolve the polymer in the mixed solvent, followed by dissolution of the beneficial agent. Some or all of the mixed solvent or a solvent component may be added to the polymer and/or the beneficial agent in order to solubilize the powder before the composition is mixed together. The various mixing steps can involve heating and/or mechanical mixing in order to form the homogeneous solution.

The amount of beneficial agent in the mixture is preferably equal to a unit dosage. A unit dosage is the amount of beneficial agent necessary to produce the desired beneficial effect in the organism to which it is administered. The absolute amount of a unit dosage can depend on many factors including, for example, the type of agent, the efficacy of the agent, the health of the organism, and the size of the organism.

The concentration of the beneficial agent can be varied, for example according to the amount of dosage required, the release rate, or the solubility of the beneficial agent. The concentration can be from 0.1 milligram per milliliter of solution (mg/ml) to 500 mg/ml, preferably from 5 mg/ml to 250 mg/ml, more preferably from 10 mg/ml to 100 mg/ml. It is preferred that the concentration of the beneficial agent is not so great that a portion of the beneficial agent separates into a separate phase from the solution.

Compositions as described may be administered in a variety of ways. Preferred methods of administration involve injection. Injection may be subcutaneous, parenteral, intramuscular, or other types of injection known to those skilled in the art. A consideration for administration by injection is the viscosity of the mixture. For example, the viscosity of the liquid is preferably sufficiently low to allow the mixture to be injected through a 20 gauge needle. Preferably the solution can be injected through a 25 gauge needle, more preferably through a 28 gauge needle, even more preferably through a 30 gauge needle, even more preferably through a 35 gauge needle. The term "needle" includes all hollow structures used for administration of a beneficial agent, including canulas and catheters. A composition can be injected through a needle when a pressure of 20 psig results in a flow of the composition of at least 1.0 milliliters/minute from the needle.

The viscosity of the liquid can be measured using a CANON-FENSKE viscometer at a temperature of 25° C. (as per ASTM D445-97). The kinematic viscosity of the liquid is preferably at most 2000 centipoise, including 2000-50 centipoise. Examples include less than 1600 centipoise, less than 1400 centipoise, less than 1200 centipoise, less than 1000 centipoise, less than 900 centipoise, less than 800 centipoise, less than 700 centipoise, less than 600 centipoise, less than 500 centipoise, less than 400 centipoise, less than 300 centipoise, less than 200 centipoise, less than 100 centipoise, and less than 50 centipoise, and all ranges therebetween.

For an implant administered by injection, the liquid mixture preferably transforms into a depot upon contact with the fluid in the body. This depot is characterized by its phase separation from the physiological fluid and its increased viscosity relative to the original liquid composition. It is this depot that serves as the polymeric implant for controlled release of the beneficial agent.

One possible mechanism for the release behavior of these compositions involves the phase separation of the beneficial agent within the implant upon administration. As the hydrophilic solvent diffuses into the aqueous surroundings, at least a portion of the beneficial agent separates into a separate phase from the rest of the depot composition. This phase separation then results in a fine suspension of the beneficial agent within the depot. Release of the beneficial agent would then occur slowly and gradually, without an initial burst release or lag time.

When the composition is administered in vivo, preferably less than 25% of the total amount of beneficial agent is released from the depot in 24 hours, more preferably less than 10% of the total amount of beneficial agent is released from the depot in 24 hours, even more preferably less than 5% of the total amount of beneficial agent is released from the depot in 24 hours, even more preferably less than 0.25% of the total amount of beneficial agent is released from the depot in 24 hours, even more preferably less than 0.05% of the total amount of beneficial agent is released from the depot in 24 hours. The organism to which the composition is administered can be, for example, a rat or a human.

The release of the beneficial agent preferably occurs over a period of days, weeks, or months. It is preferred that at least 25% of the total amount of beneficial agent is released within one year of administration, more preferably at least 25% of the total amount of the beneficial agent is released within one month of administration, most preferably at least 25% of the total amount of the beneficial agent is released within one week of administration. Alternatively, it is preferred that at least 20% of the total amount of beneficial agent is released within one year of administration, more preferably at least 20% of the total amount of the beneficial agent is released within one month of administration, most preferably at least 20% of the total amount of the beneficial agent is released within one week of administration. The desired length of the release period will vary according to the physiological treatment desired.

Figure 1:
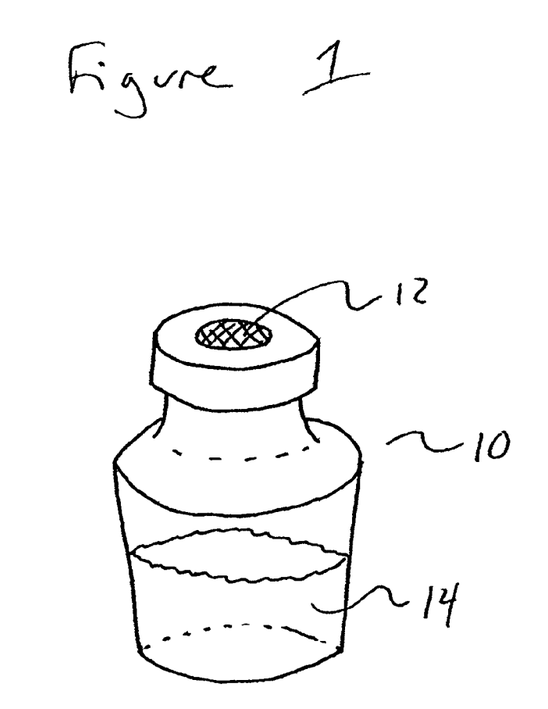
FIG. 1 is a view of a vial containing an injectable composition.

The composition may be conveniently packaged in a sterile container, such as the vial 10 illustrated in FIG. 1. This container may be part of a kit which may optionally contain a sterile syringe and needle. The vial 10 may be sealed with a septum 12. This septum seals the liquid 14 and may be pierced by a needle and syringe to permit withdrawal of the mixture. The vial may contain all the ingredients necessary for the controlled release of the beneficial agent. The liquid composition in the vial preferably contains a unit dosage of the beneficial agent. It is preferred that the end user of the mixture not be required to add further ingredients or to measure the dosage prior to administration. The liquid composition may be contained in a syringe such that it can be directly administered by injection.

Alternatively, the composition may be packaged in more than one container. For example, a solution of polymer in a solvent or solvent mixture may be in one vial, and a solution of the beneficial agent in a solvent or solvent mixture may be in another vial. The solvents and/or solvent mixture may be the same or different. The contents of the vials may be combined and mixed, and the final composition administered by injection. In another example, the beneficial agent and polymer may be in one container, and the solvent mixture may be in another container. The beneficial agent and polymer may be provided together as a powder, or the beneficial agent and polymer may be provided together as a tablet or capsule. The beneficial agent and polymer may be combined with the solvent mixture such that the polymer and beneficial agent dissolve, and the final composition administered by injection. In another example, the polymer may be provided as a solution in the solvent mixture in a vial, and the beneficial agent may be provided in a separate container. Alternatively, the beneficial agent may be provided as a solution in the solvent mixture in a vial, and the polymer may be provided in a separate container. The contents of the containers may be combined such that a liquid formulation is formed, and the final composition administered by injection.

Preferably, the packaging of the composition or its components is disposable, more preferably recyclable. It is preferred that the composition and its packaging are sterile.

EXAMPLES

Examples 1-5

In these examples, compositions containing protein were prepared such that they could be easily administered by injection, yet would provide for a gradual, controlled release of the protein. Release behaviors (release profile) of rhGH (GENENTECH, S. San Francicso, Calif.) from the compositions were studied both in vivo and in vitro by measuring the amount of protein released as a function of time. The stability of the protein was determined by measuring the percentage of the released protein which had not aggregated. A higher percentage of non-aggregated protein indicated better stability.

Poly(L-lactic acid) (PLA) was obtained from BOEHRINGER INGELHEIM, Ridgefield, Conn., as RESOMER 202H, with a reported molecular weight of 12,000 daltons. Polymer solutions were prepared by mixing the benzyl alcohol and benzyl benzoate to form a homogenous mixture. PLA was then added to this mixture and was dissolved by gentle mixing with a vortex mixer. The rhGH was complexed with zinc (10 moles Zn/mole protein), and powders of the complexed protein, sucrose, and surfactant were prepared using a bench top spray dryer.

The relative amounts of ingredients used for making the protein powders and the polymer solutions are given in Tables 1 and 2 respectively. For Examples 1-4, the appropriate protein powder was dissolved in the polymer solution to give an overall concentration of 50 mg/ml of protein. For Example 5, the appropriate protein powder was dissolved in the polymer solution to give an overall concentration of 100 mg/ml of protein. Dissolution was accomplished by gentle mixing with a vortex mixer followed by homogenization at 8000 rpm for 2 minutes, using a 5-mm fine screen shear homogenizer to ensure a uniform solution. The resulting solutions could be injected through a 25-gauge needle.

TABLE 1

| Protein Formulation | Concentrations (mg/mL) | | | Protein Content (wt %) |
|---|---|---|---|---|
| | Protein | Sucrose | Tween 20 | |
| A | 20.0 | 2.0 | 0.05 | 60.0 |
| B | 20.0 | 5.0 | 0.05 | 50.0 |

TABLE 2

| Example | Polymer Solution (wt %) | | | Protein Formulation | % Release in 24 hr | % Non-aggregated protein** |
|---|---|---|---|---|---|---|
| | PLA | Benzyl Alcohol | Benzyl Benzoate | | | |
| 1 | 20 | 5 | 75 | A* | 3.8 | 99.6 |
| 2 | 20 | 5 | 75 | B* | 1.4 | 73.0 |
| 3 | 30 | 5 | 65 | A* | — | — |
| 4 | 30 | 5 | 65 | B* | — | — |
| 5 | 20 | 5 | 75 | B*** | 0.6 | 85.5 |

*Added to polymer solution at a concentration of 50 mg/mL
**Determined by SEC-HPLC
***Added to polymer solution at a concentration of 100 mg/mL For in vitro release studies, 100 microliter (μL) samples of the resulting liquid were placed in 1.5 mL of release buffer and held at 37° C. for 24 hours. The release buffer was 50 mM HEPES, 5 mM EDTA, 0.1 mM $NaN_3$, with a pH of 8.0. The entire release medium was then analyzed by size exclusion chromatography—high performance liquid chromatography (SEC-HPLC) to determine total protein content and percentage of non-aggregated protein present, using a method similar to that described in Maa et. al., J. Pharm Sci. 2 (87) 152-159, 1998. The SEC-HPLC was run using a 7.8×300 mm TSK 2000-SWXL column at room temperature, with a mobile phase of 50 mM $NaH_2PO_4$, 150 mM NaCl, pH 7.2. The flow rate was 1.0 ml/min, and the run time was 20 min. Protein (10 μg) was injected and the eluent monitored for absorbance at 214 nm. The results of in vitro release after 24 hours are given in Table 2.

Figure 2:
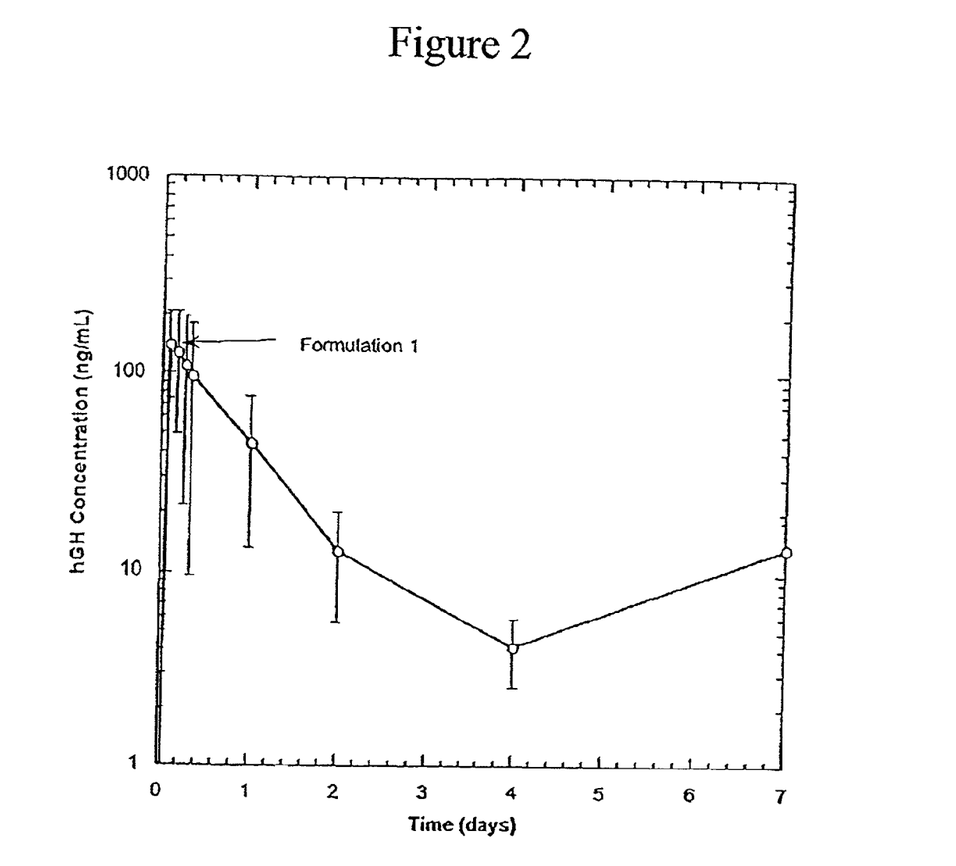
FIGS. 2-4 are graphs illustrating the release of rhGH over time.
Figure 3:
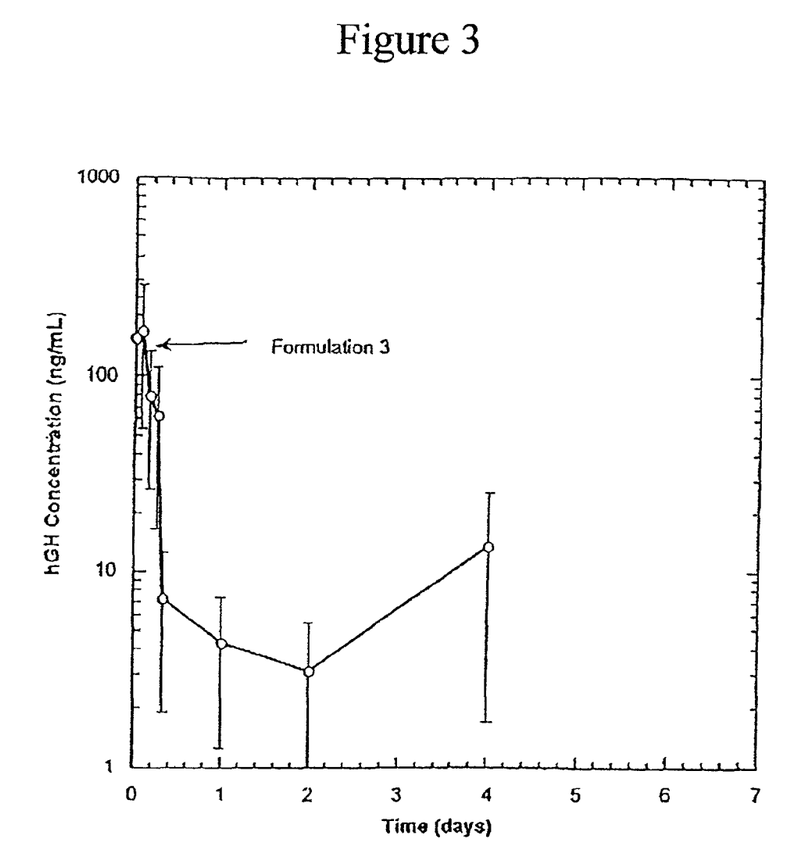
Figure 4:
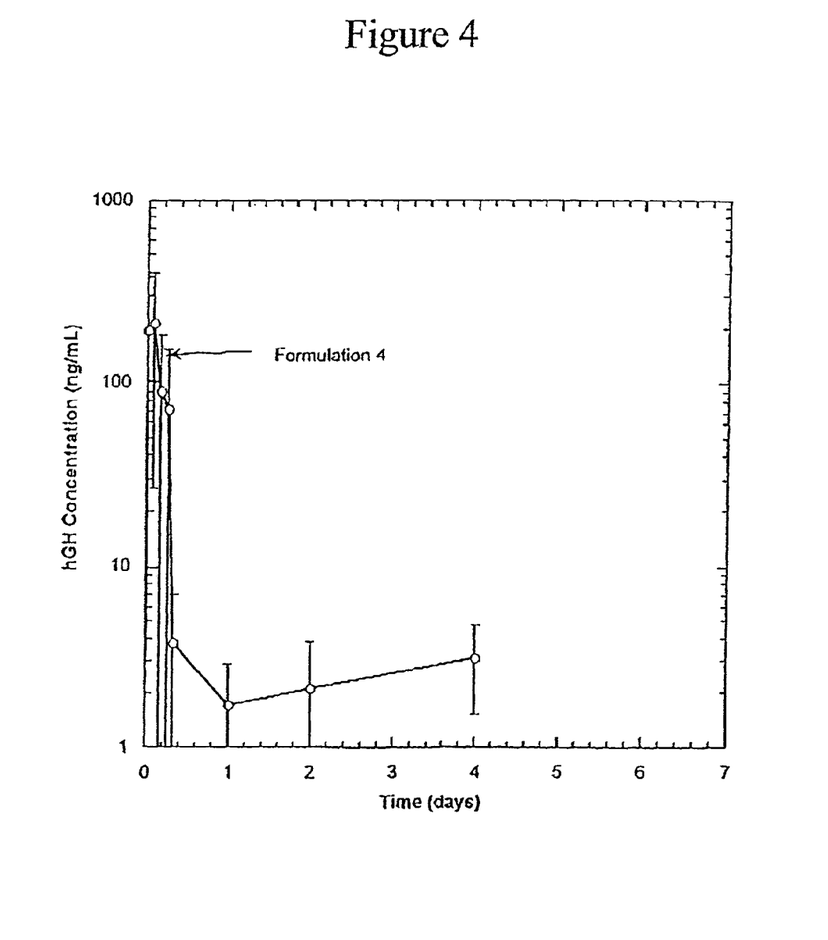

Release profiles of the protein from the compositions in vivo were examined by pharmacokinetic studies. In these studies, SD rats were injected with a liquid composition at 5 milligrams protein/kilogram body weight (mg/kg) and 15 mg/kg. Injections were through 25-gauge needles. Serum samples were collected at the time of injection (time=0 hr) and then at the time intervals of 2, 4, 6, 8, 24, 96, and 168 hours. The serum samples were analyzed for rhGH by a specific rhGH ELISA (GENENTECH ASSAY SERVICES), having an assay detection limit of 0.1 nanograms per milliliter (ng/mL), to determine the concentration of rhGH in each sample. This protein concentration is due to the release of the protein from the implant. The resulting graphs of protein release over time are illustrated in FIGS. 2-4 for Examples 1, 3, and 4.

Figure 6:
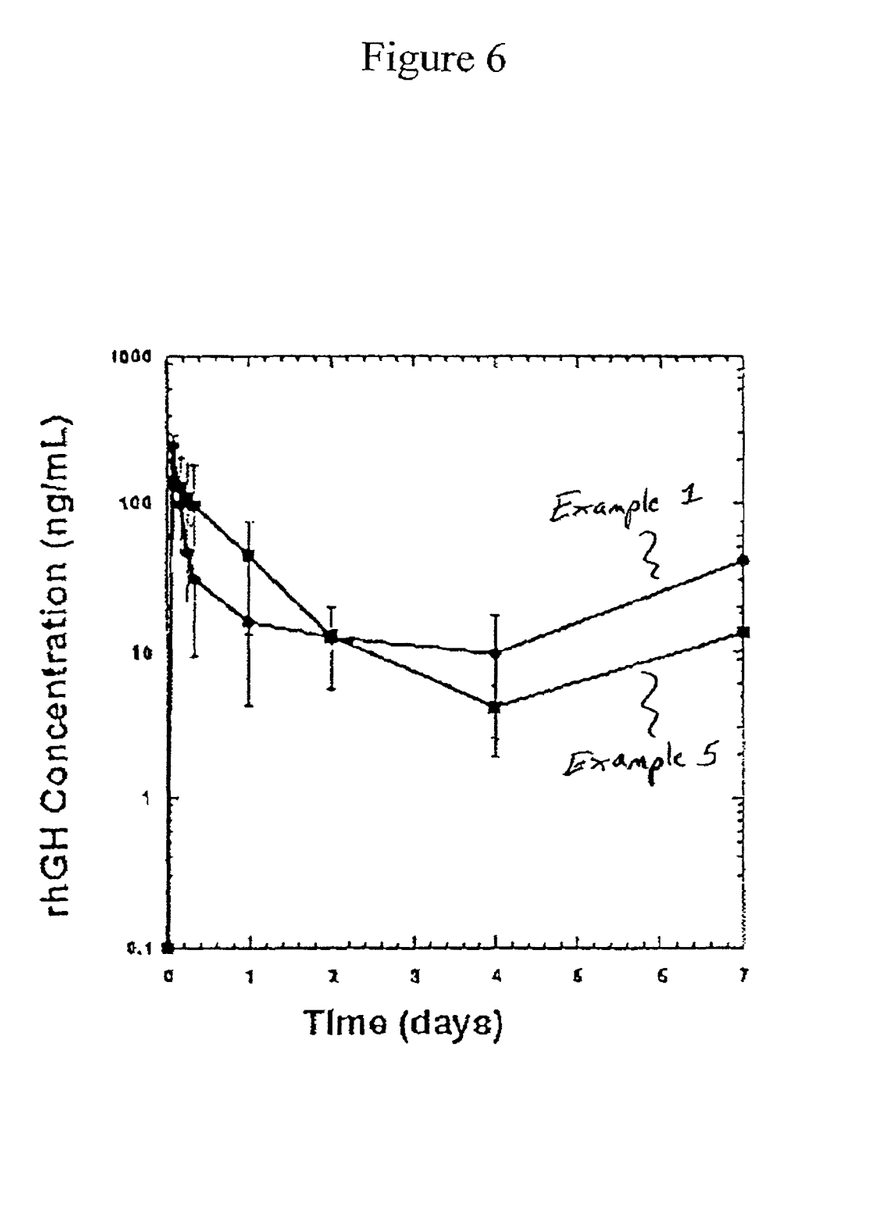
FIG. 6 is a graph illustrating the release of rhGH over time.

A comparative graph of Examples 1 and 5 is illustrated in FIG. 6. In Example 1, a rapid rise in serum rhGH level was observed, and this was followed by a gradual decline to a plateau of 9 ng/mL after 4 days. In Example 5, a rapid rise in serum rhGH level was followed by a rapid decline to a plateau of 20 ng/mL after 24 hours. The pharmacokinetic data for these examples are given in Table 3.

TABLE 3

| | | rhGH Levels in Serum | | |
|---|---|---|---|---|
| Example | Protein Formulation | Maximum (ng/mL) | Average 0-2 days (ng * day/mL) | Average 0-7 days (ng * day/mL) |
| 1 | A (50 mg/mL) | 172.1 | 123.3 | 163.9 |
| 5 | B (100 mg/mL) | 249.0 | 64.5 | 163.1 |

Example 6

In this example, an injectable composition for controlled release of a protein was prepared. Release profiles of the protein from the composition were studied both in vivo and in vitro by measuring the amount of protein released as a function of time.

An aqueous protein solution was prepared by mixing VEGF (10 mg/ml), sucrose (10 mg/ml), 0.03% POLYSORBATE 80, and histidine (10 mM). The solution had a pH of 6.0. This protein solution was sprayed into liquid nitrogen using an ultrasonic nebulizer, as described in U.S. Pat. No. 5,019,400. The resulting frozen protein droplets were then lyophilized to produce particles having a diameter of 2-10 μm. The protein powder was mixed into a polymer solution composed of 30 wt % PLA, 69 wt % benzyl benzoate, and 1 wt % benzyl alcohol. The mixture was made by homogenization at 8,000 rpm for 2 minutes. The resulting mixture contained 12 mg protein per milliliter of liquid.

For in vitro release studies, 100 microliter (μl) samples were injected into 1.5 ml of a release buffer and held at 37° C. The release buffer was an aqueous mixture having a pH of 7.0, containing 10 mM histidine, 140 mM NaCl, 0.02% POLYSORBATE 20, and 0.02% sodium azide. At given intervals of time, the entire release medium was replaced with fresh buffer, the medium was then analyzed by SEC-HPLC to determine total protein content. The SEC-HPLC was run using a 7.8×300 mm TSK 300-SW column, having 5 μm particles, at room temperature. The mobile phase was 25 mM $NaH_2PO_4$, 1.0 M NaCl with a of pH 7.4. The flow rate was 1.0 mL/min, and the run time was 20 min. Protein (25 μg) was injected and the eluent monitored for absorbance at 214 nm.

After 24 hours at 37° C., approximately 0.2% of the VEGF had been released. After an additional 168 hours, approximately 0.1% more of the VEGF was released.

Figure 5:
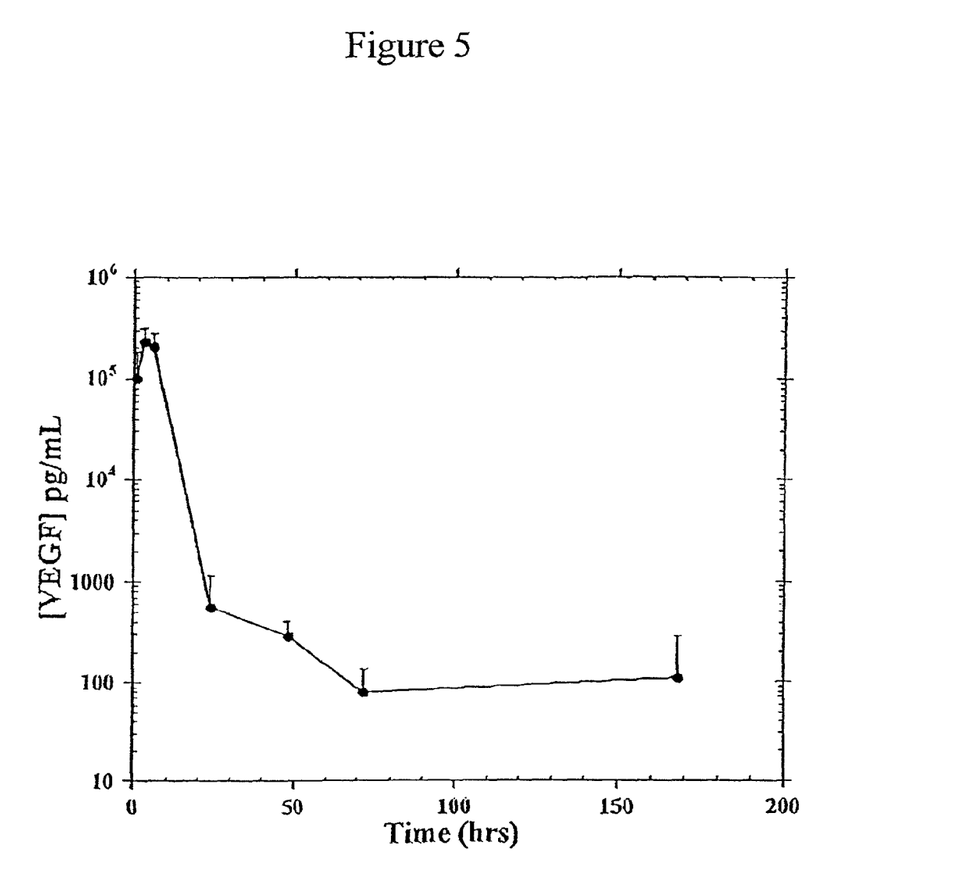
FIG. 5 is a graph illustrating the release of rhVEGF over time.

The release profile of the protein from the composition in vivo was examined by pharmacokinetic studies. In this study, SD rats weighing between 265 g and 302 g were injected with a liquid composition at 3.6 mg/kg (dose volume of 0.3 ml/kg). Injections were through 25-gauge needles. Whole blood was collected from the rats in EDTA-treated microtainers and plasma harvested. The plasma samples were frozen until analysis and were then assayed using a VEGF ELISA to determine the concentration of VEGF in each sample. This protein concentration is due to the release of the protein from the implant. The resulting graph of protein release over time is illustrated in FIG. 5. The initial plasma levels of rhVEGF were above 100 nanograms per milliliter (ng/ml) until 24 hours, after which the level remained around 100 picograms per milliliter (pg/ml) until 168 hours.

Obviously, numerous modifications and variations of the present invention are possible in light of the above teachings. It is therefore to be understood that within the scope of the appended claims, the invention may be practiced otherwise than as specifically described herein.

The invention claimed is:

1. A composition for administration of a beneficial agent to an organism, comprising:
   a solvent mixture, comprising
      a hydrophobic solvent; and
      a hydrophilic solvent;
   a bioerodible polymer; and
   a beneficial agent,
   wherein the polymer and the beneficial agent are dissolved, and wherein the hydrophobic solvent has a solubility in water of less than 1 wt %.

2. The composition of claim 1, wherein at least 55 wt % of the solvent mixture is the hydrophobic solvent.

3. The composition of claim 1, wherein at least 90 wt % of the solvent mixture is the hydrophobic solvent.

4. The composition of claim 1, wherein the hydrophobic solvent has a solubility in water of less than 0.1 wt %.

5. The composition of claim 1, wherein the beneficial agent has a concentration from 0.1 mg/ml to 500 mg/ml.

6. The composition of claim 1, wherein the beneficial agent has a concentration from 10 mg/ml to 100 mg/ml.

7. The composition of claim 1, wherein the composition can be injected through a 20 to 35 gauge needle.

8. The composition of claim 1, wherein the composition can be injected through a 25 to 30 gauge needle.

9. The composition of claim 1, wherein the composition can be injected through a 25-gauge needle.

10. The composition of claim 1, wherein the composition can be injected through a 28-gauge needle.

11. The composition of claim 1, wherein the composition can be injected through a 30-gauge needle.

12. The composition of claim 1, wherein the viscosity of the composition is less than 2000 centipoise.

13. The composition of claim 1, wherein less than 25% of the beneficial agent is released in 24 hours following administration in vivo.

14. The composition of claim 1, wherein the hydrophobic solvent is benzyl benzoate, the hydrophilic solvent is benzyl alcohol, the bioerodible polymer is polylactide, and the beneficial agent is a peptide or protein.

15. The composition of claim 1, wherein the hydrophilic solvent, the hydrophobic solvent, the bioerodible polymer, and the beneficial agent form a suspension.

16. The composition of claim 1, wherein the hydrophilic solvent, the hydrophobic solvent, the bioerodible polymer, and the beneficial agent form a solution.

17. A composition for administration of a beneficial agent, comprising:
   a solvent mixture, comprising
      a hydrophobic solvent; and
      a hydrophilic solvent;
   a bioerodible polymer; and
   a beneficial agent,
wherein the viscosity of the composition is less than 2000 centipoise, and wherein the hydrophobic solvent has a solubility in water of less than 1 wt %.

18. The composition of claim 17, wherein at least 55 wt % of the solvent mixture is the hydrophobic solvent.

19. The composition of claim 17, wherein at least 90 wt % of the solvent mixture is the hydrophobic solvent.

20. The composition of claim 17, wherein the hydrophobic solvent has a solubility in water of less than 0.1 wt %.

21. The composition of claim 17, wherein the composition can be injected through a 20 to 35 gauge needle.

22. The composition of claim 17, wherein the composition can be injected through a 25-gauge needle.

23. The composition of claim 17, wherein the composition can be injected through a 28-gauge needle.

24. The composition of claim 17, wherein the composition can be injected through a 30-gauge needle.

25. The composition of claim 17, wherein the viscosity of the composition is less than 500 centipoise.

26. The composition of claim 17, wherein the hydrophobic solvent is benzyl benzoate, the hydrophilic solvent is benzyl alcohol, the bioerodible polymer is polylactide, and the beneficial agent is a peptide or protein.

27. The composition of claim 17, wherein the hydrophilic solvent, the hydrophobic solvent, the bioerodible polymer, and the beneficial agent form a solution.

28. The composition of claim 17, wherein the hydrophilic solvent, the hydrophobic solvent, the bioerodible polymer, and the beneficial agent form a suspension.

29. A composition for administration of a beneficial agent to an organism, comprising:
   a solvent mixture, the solvent mixture comprising a hydrophobic solvent and a hydrophilic solvent;
   a bioerodible polymer dissolved in the solvent mixture; and
   a beneficial agent dissolved in the solvent mixture,
   wherein the viscosity of the composition is less than 2000 centipoise, at least 90 wt % of the solvent mixture is the hydrophobic solvent, the hydrophobic solvent has a solubility in water of less than 0.1 wt %, and less than 25% of the beneficial agent is released in 24 hours following administration in vivo.

30. The composition of claim 29, wherein the hydrophobic solvent is benzyl benzoate, the hydrophilic solvent is benzyl alcohol, the bioerodible polymer is polylactide, and the beneficial agent is a peptide or protein.

31. A method of administering a beneficial agent, comprising: injecting the composition of claim 1 into an organism through a needle.

32. The method of claim 31, wherein the needle is a 20 to 35 gauge needle.

33. The method of claim 31, wherein the needle is a 25 to 30 gauge needle.

34. The method of claim 31, wherein the needle is a 25-gauge needle.

35. The method of claim 31, wherein the needle is a 28-gauge needle.

36. The method of claim 31, wherein the needle is a 30-gauge needle.

37. A method of administering a beneficial agent, comprising: injecting the composition of claim 17 into an organism through a needle.

38. The method of claim 37, wherein the needle is a 20 to 35 gauge needle.

39. The method of claim 37, wherein the needle is a 25-gauge needle.

40. The method of claim 37, wherein the needle is a 28-gauge needle.

41. The method of claim 37, wherein the needle is a 30-gauge needle.

42. A method of administering a beneficial agent, comprising: injecting the composition of claim 29 into an organism through a needle.

43. The composition of claim 12, wherein the viscosity of the composition is less than 900 centipoise.

44. The composition of claim 43, wherein the viscosity of the composition is less than 500 centipoise.

45. The composition of claim 44, wherein the viscosity of the composition is less than 44 centipoise.

46. The composition of claim 45, wherein the viscosity of the composition is less than 200 centipoise.

47. The composition of claim 17, wherein the viscosity of the composition is less than 900 centipoise.

48. The composition of claim 25, wherein the viscosity of the composition is less than 200 centipoise.

* * * * *